(12) United States Patent
Tsuge

(10) Patent No.: US 11,701,497 B2
(45) Date of Patent: Jul. 18, 2023

(54) GUIDE WIRE

(71) Applicant: ASAHI INTECC CO., LTD., Aichi (JP)

(72) Inventor: Kenta Tsuge, Seto (JP)

(73) Assignee: ASAHI INTECC CO., LTD., Aichi (JP)

( * ) Notice: Subject to any disclaimer, the term of this patent is extended or adjusted under 35 U.S.C. 154(b) by 0 days.

(21) Appl. No.: 17/979,006

(22) Filed: Nov. 2, 2022

(65) Prior Publication Data

US 2023/0090889 A1 Mar. 23, 2023

Related U.S. Application Data

(63) Continuation of application No. 16/846,446, filed on Apr. 13, 2020, now Pat. No. 11,541,210, which is a (Continued)

(51) Int. Cl.
*A61M 25/09* (2006.01)

(52) U.S. Cl.
CPC ..... *A61M 25/09* (2013.01); *A61M 2025/0915* (2013.01); *A61M 2025/09083* (2013.01); (Continued)

(58) Field of Classification Search
CPC ........ A61M 25/09; A61M 2025/09083; A61M 2025/09141; A61M 2025/0915; (Continued)

(56) References Cited

U.S. PATENT DOCUMENTS 6,612,998 B2 9/2003 Gosiengfiao et al.
7,455,646 B2 11/2008 Richardson et al.
(Continued)

FOREIGN PATENT DOCUMENTS

CN 103830830 A 6/2014
EP 2732846 A1 5/2014
(Continued)

OTHER PUBLICATIONS

International Search Report and Written Opinion dated Nov. 28, 2017 for PCT/JP2017/037002 filed on Oct. 12, 2017, 8 pages.
Office Action dated Jun. 21, 2022, for the corresponding U.S. Appl. No. 16/846,450.

*Primary Examiner* — James D Ponton
*Assistant Examiner* — Neeraja Gollamudi
(74) *Attorney, Agent, or Firm* — Xsensus LLP

(57) ABSTRACT

A guide wire of the present disclosure includes a core shaft having a distal end portion decreasing in cross-sectional area, a coil body wound to cover the distal end portion, and a distal end fixing portion fixing the core shaft and the coil body to each other. The distal end portion includes a small cross-sectional area portion, a large cross-sectional area portion, and a tapered portion between the small cross-sectional area portion and the large cross-sectional area portion. The core shaft and the coil body are fixed at a portion excluding the tapered portion. A first bending rigidity FR1 of the large cross-sectional area portion, a second bending rigidity FR2 of the small cross-sectional area portion, and a length L of the tapered portion satisfy the following expressions (1) and (2). In the following expressions (1) and (2), the unit of L is mm (millimeter).

$$(FR1/FR2)^{0.25}/L \geq 0.83 \qquad (1)$$

$$1 \leq L \leq 3 \qquad (2)$$

20 Claims, 8 Drawing Sheets

Related U.S. Application Data continuation of application No. PCT/JP2017/037002, filed on Oct. 12, 2017.

(52) U.S. Cl.
CPC .............. *A61M 2025/09141* (2013.01); *A61M 2025/09166* (2013.01); *A61M 2025/09175* (2013.01)

(58) Field of Classification Search
CPC ......... A61M 2025/09166; A61M 2025/09175; A61M 2025/09058
See application file for complete search history.

(56) References Cited

U.S. PATENT DOCUMENTS

| | | |
|---|---|---|
| 2003/0069521 A1 | 4/2003 | Reynolds et al. |
| 2003/0100848 A1 | 5/2003 | Gosiengfiao et al. |
| 2004/0106878 A1 | 6/2004 | Skujins et al. |
| 2004/0167440 A1 | 8/2004 | Sharrow et al. |
| 2007/0112282 A1 | 5/2007 | Skujins et al. |
| 2007/0282225 A1 | 12/2007 | Terashi et al. |
| 2008/0262474 A1 | 10/2008 | Northrop |
| 2009/0227900 A1 | 9/2009 | Kim et al. |
| 2014/0142557 A1 | 5/2014 | Kosugi et al. |
| 2014/0350519 A1 | 11/2014 | Urie |
| 2015/0148706 A1 | 5/2015 | Abner |
| 2016/0346518 A1* | 12/2016 | Terashi ................. A61M 25/09 |
| 2020/0237355 A1 | 7/2020 | Tsuge et al. |

FOREIGN PATENT DOCUMENTS

| | | |
|---|---|---|
| JP | 6-54912 A | 3/1994 |
| JP | 7-80076 A | 3/1995 |
| JP | 2010-524588 A | 7/2010 |
| JP | 2011-000469 A | 1/2011 |
| JP | 2016-221198 A | 12/2016 |
| JP | 2017-500925 A | 1/2017 |
| WO | 2005/030311 A1 | 4/2005 |
| WO | 2010/108308 A1 | 9/2010 |
| WO | 2015/080948 A1 | 6/2015 |

* cited by examiner

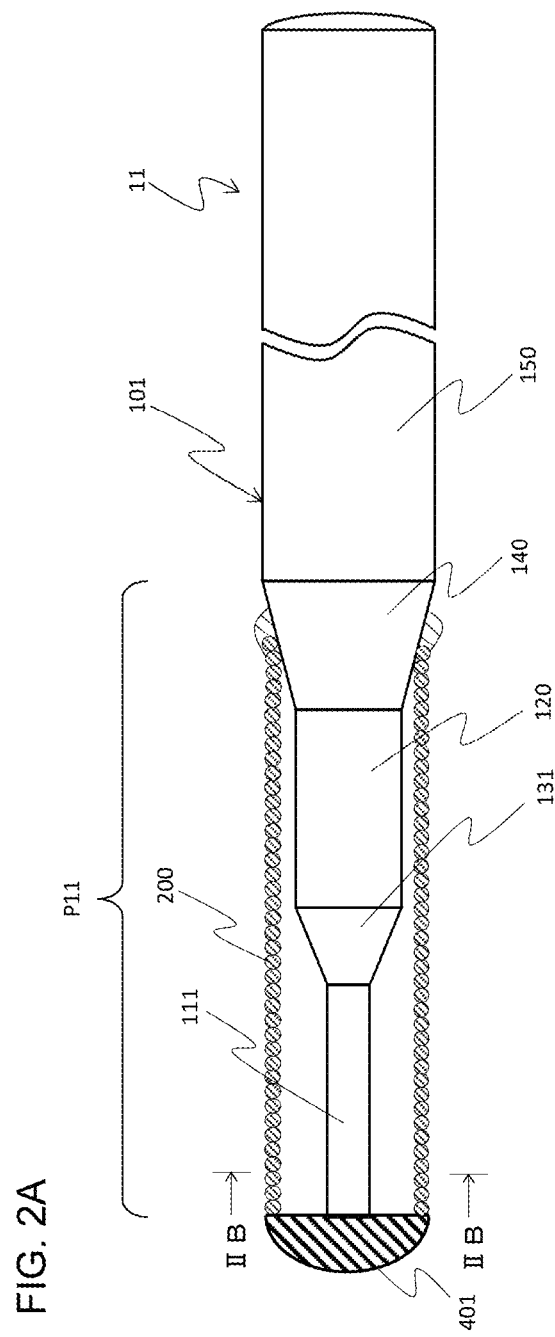

GUIDE WIRE

CROSS-REFERENCE TO RELATED APPLICATIONS

This application is a continuation application of U.S. application Ser. No. 16/846,446, filed Apr. 13, 2020, which is a continuation application of International Application No. PCT/JP2017/037002, filed Oct. 12, 2017. The contents of these applications are incorporated herein by reference in their entirety.

TECHNICAL FIELD

The present disclosure relates to a guide wire.

BACKGROUND

For example, when treating an occlusion site (for example, chronic total occlusion: CTO) in a blood vessel caused by the progress of calcification, a guide wire for guiding a treatment instrument such as a balloon catheter is inserted prior to the treatment instrument.

As such a guide wire to be inserted into a blood vessel or the like, there has been proposed a guide wire in which the distal end portion of a core shaft serving as a shaft is stepwisely reduced in diameter so that the distal end can be flexibly bent in accordance with the shape of the inside of the blood vessel, according to WO 2015/080948.

In this technique, the distal end portion is stepwisely reduced in diameter, resulting in one or more inflection points. When the distal side of the inflection point is bent, a loop of the guide wire can be formed.

SUMMARY

However, when the conventional guide wire as described above is used for a lesion such as a stenosis or an occlusion in a blood vessel, excessive force may be applied to the inflection point due to large counteraction when pushing the stenosis or the like. For this reason, the core shaft may be broken at the inflection point, and the sharp edge generated by the break causes perforation or dissociation of the blood vessel, and the bend forming the loop exceeds the inflection point to be displaced to a tapered portion or a large diameter portion in the proximal end direction. This may cause plastic deformation at a portion with high rigidity, disabling reuse of the guide wire.

The present disclosure has been made in view of the above circumstances. One or more embodiments provide a guide wire capable of preventing breakage of the core shaft from the tapered portion as a starting point, while suppressing displacement of the bend of the core shaft beyond the tapered portion to the proximal end direction and other problems.

In one broad aspect, a guide wire according to an embodiment of the present disclosure includes a core shaft that includes a distal end portion stepwisely decreasing in cross-sectional area toward a distal end direction, a coil body wound to cover at least a part of an outer periphery of the cross-sectional area-decreased distal end portion, a distal end fixing portion that fixes the distal end of the core shaft, and a distal end of the coil body to each other. The distal end portion of the core shaft includes a small cross-sectional area portion adjacent to the distal end fixing portion, a large cross-sectional area portion further in a proximal end direction than the small cross-sectional area portion and has a larger cross-sectional area than the small cross-sectional area portion, and a tapered portion between the small cross-sectional area portion and the large cross-sectional area portion and gradually increases in cross-sectional area from the small cross-sectional area portion toward the large cross-sectional area portion. The core shaft and the coil body are fixed at a portion of the core shaft excluding the tapered portion, and a first bending rigidity FR1 of the large cross-sectional area portion, a second bending rigidity FR2 of the small cross-sectional area portion, and a length L of the tapered portion in an axial direction of the core shaft satisfy the following expressions (1) and (2), $$(FR1/FR2)^{0.25}/L \geq 0.83 \tag{1}$$

$$1 \leq L \leq 3 \tag{2}$$

(in the above expressions (1) and (2), the unit of L is mm (millimeter).)

In another broad aspect, a guide wire according to an embodiment of the present disclosure includes a core shaft that includes a distal end portion stepwisely decreasing in diameter toward a distal end direction, a coil body wound to cover at least a part of an outer periphery of the diameter-decreased distal end portion, a distal end fixing portion that fixes a distal end of the core shaft, and a distal end of the coil body to each other. The distal end portion of the core shaft includes a small diameter portion adjacent to the distal end fixing portion, a large diameter portion further in a proximal end direction than the small diameter portion and has a larger diameter than the small diameter portion, and a tapered portion between the small diameter portion and the large diameter portion and gradually increases in diameter from the small diameter portion toward the large diameter portion. The core shaft and the coil body are fixed at a portion of the core shaft excluding the tapered portion, and a diameter D2 of the large diameter portion, a diameter D1 of the small diameter portion, and a length L of the tapered portion in an axial direction of the core shaft satisfy the following expressions (7) and (8), $$(D2/D1)/L \geq 0.83 \tag{7}$$

$$1 \leq L \leq 3 \tag{8}$$

(in the above expressions (7) and (8), the unit of L is mm (millimeter)).

BRIEF DESCRIPTION OF DRAWINGS

FIG. 2A is a schematic section view illustrating another guide wire, according to some embodiments of the present disclosure.

DETAILED DESCRIPTION

Figure 1:
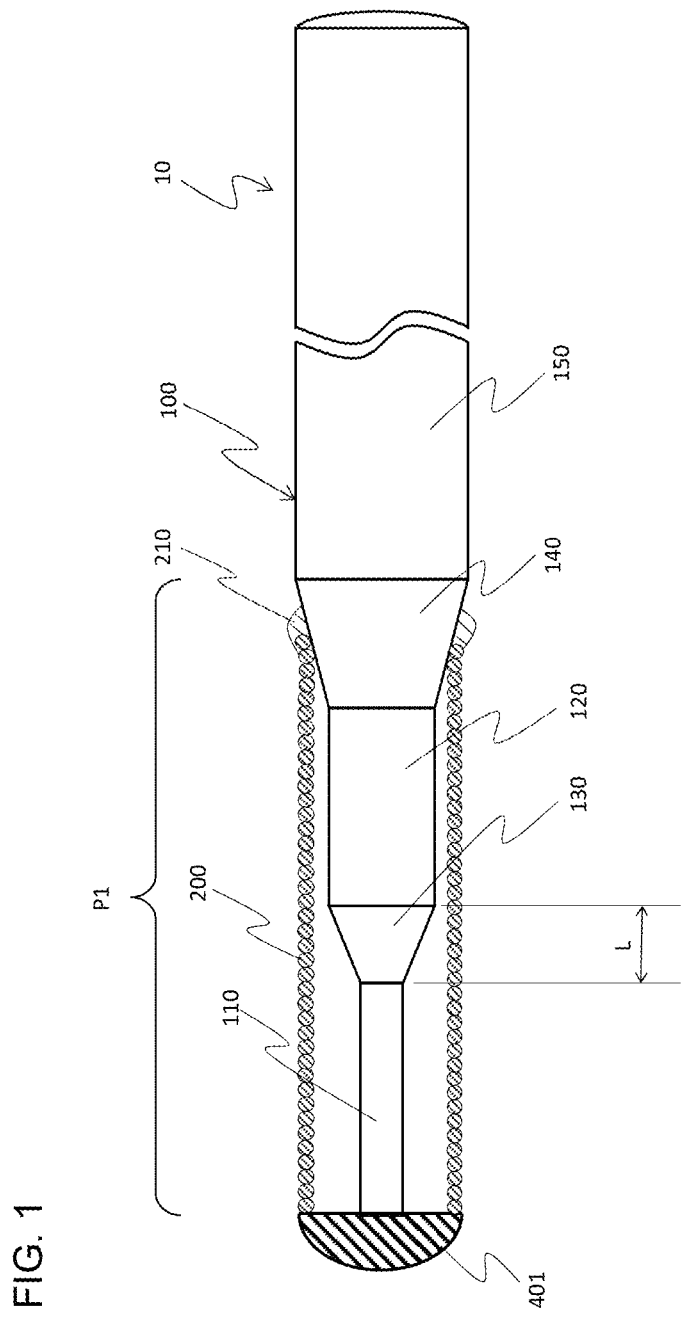
FIG. 1 is a schematic section view illustrating a guide wire, according to some embodiments of the present disclosure.

As used herein, an element or step recited in the singular and proceeded with the word "a" or "an" should be understood as not excluding plural elements, unless such exclusion is explicitly recited. Furthermore, references to "one embodiment" of the present invention are not intended to be interpreted as excluding the existence of additional embodiments that also incorporate the recited features.

In addition, in the description, the wording "cross-sectional area" can be replaced with "diameter" hereinafter, excluding those in paragraph [0012] and [0018]. For example, "small cross-sectional area portion" may be read "small diameter portion", and "large cross-sectional area portion" may be read "large diameter portion".

Note that in the specification, "distal end direction" is a direction along the axial direction of the guide wire and indicates a direction of the side on which the distal end fixing portion is positioned relative to the large cross-sectional area portion of the core shaft. The "proximal end direction" is a direction along the axial direction of the guide wire and indicates the direction opposite to the distal end direction.

A guide wire of the present disclosure includes a core shaft that includes a distal end portion stepwise decreasing in cross-sectional area toward a distal end direction, a coil body wound to cover at least a part of an outer periphery of the cross-sectional area-decreased distal end portion, and a distal end fixing portion that fixes the distal end of the core shaft, and a distal end of the coil body to each other. The distal end portion of the core shaft includes a small cross-sectional area portion adjacent to the distal end fixing portion, a large cross-sectional area portion that is positioned in a proximal end direction than the small cross-sectional area portion and has an outer cross-sectional area larger than an outer cross-sectional area of the small cross-sectional area portion, and a tapered portion between the small cross-sectional area portion and the large cross-sectional area portion and gradually increasing in cross-sectional area from the outer cross-sectional area of the small cross-sectional area portion toward the outer cross-sectional area of the large cross-sectional area portion. The core shaft and the coil body are fixed at a portion of the core shaft excluding the tapered portion. A first bending rigidity FR1 of the large cross-sectional area portion, a second bending rigidity FR2 of the small cross-sectional area portion, and a length L of the tapered portion in an axial direction of the core shaft satisfy the following expressions (1) and (2):

$$(FR1/FR2)^{0.25}/L \geq 0.83 \quad (1)$$

$$1 \leq L \leq 3 \quad (2)$$

(In the above expressions (1) and (2), the unit of L is mm (millimeter).)

Hereinafter, embodiments of the present disclosure will be described with reference to the enclosed drawings. However, the disclosure is not limited only to the embodiments illustrated in the drawings.

FIG. 1 is a schematic front view illustrating a guide wire, according to some embodiments of the present disclosure. A guide wire 10 roughly includes a core shaft 100, a coil body 200, and a distal end fixing part 401, as illustrated in FIG. 1.

The core shaft 100 has a distal end portion P1 stepwisely reducing or decreasing in cross-sectional area toward a distal end direction. The distal end portion P1 of the core shaft 100 includes a small cross-sectional area portion 110 that is adjacent to, e.g., continuous with, the distal end fixing portion 401 described later, a large cross-sectional area portion 120 further in a proximal end direction than the small cross-sectional area portion 110 and has a larger outer cross-sectional area than an outer cross-sectional area of the small cross-sectional area portion 110, and a tapered portion 130 between, e.g., continuous with, the small cross-sectional area portion 110 and the large cross-sectional area portion 120. The tapered portion 130 gradually increases in cross-sectional area from the small cross-sectional area portion 110 toward the large cross-sectional area portion 120. Specifically, in a state where the core shaft 100 extends in a straight line, for example, the section shape orthogonal to the axial direction of the core shaft 100 (section shape) of each of the small cross-sectional area portion 110 and the large cross-sectional area portion 120 is circular with a certain cross-sectional area in the axial direction, and the section shape of the tapered portion 130 is a truncated conical shape. Further, the core shaft 100 includes a truncated conical connection portion 140 whose distal end is adjacent to, e.g., continuous with, the proximal end of the large cross-sectional area portion 120 and a core shaft main body 150 whose distal end is adjacent to, e.g., continuous with, the proximal end of the connection portion 140. In particular, the connection portion 140 may be tapered continuously with the large cross-sectional area portion 120 and the core shaft main body 150 and increases in cross-sectional area from the large cross-sectional area portion 120 toward the core shaft main body 150.

Figure 2B:
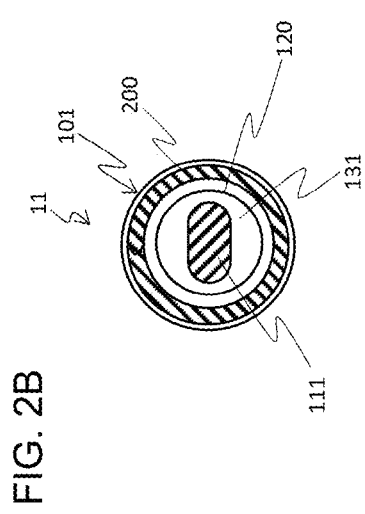
FIG. 2B is a schematic section view taken along line IIB-IIB of FIG. 2A.

Note that the section shape of the above-described small cross-sectional area portion 110 may be a flat shape, e.g., a shape that provides a flat surface, such as an elliptical rather than a circular shape (for example, see a small cross-sectional area portion 111 of a core shaft 101 illustrated in FIGS. 2A and 2B). Thus, the bend of the distal end portion P11 of the core shaft 101 can be guided in a direction perpendicular to the flat surface of the small cross-sectional area portion 111 that is easily deformed, which allows the guide wire 11 to be securely controlled during the procedure.

The total length of the core shaft 100 may be 1,800 to 3,000 mm, e.g., 1,900 to 2,500. The axial length of the distal end portion of the core shaft 100 may be 200 to 1,000 mm, e.g., 300 to 850 mm. The outer diameter of the core shaft main body 150 may be 0.25 to 0.5 mm, and the outer diameter of the large cross-sectional area portion 120 may be $1/5$ to $2/5$ of the core shaft main body 150. which corresponds to $(1/5)^2$ to $(2/5)^2$ in area ratio. Note that the outer cross-sectional area of the small cross-sectional area portion 110 is selected as described below.

Here, the outer cross-sectional areas of the large cross-sectional area portion 120 and the small cross-sectional area portion 110, and the length of the tapered portion 130 are selected so that the first bending rigidity FR1 of the large cross-sectional area portion, the second bending rigidity FR2 of the small cross-sectional area portion, and the length L of the tapered portion 130 in the axial direction of the core shaft satisfy the following expressions (1) and (2). In the following expressions (1) and (2), the unit of L is mm (millimeter).

$$(FR1/FR2)^{0.25}/L \geq 0.83 \quad (1)$$

$$1 \leq L \leq 3 \quad (2)$$

Alternatively, the first bending rigidity FR1 of the large cross-sectional area portion, the second bending rigidity FR2 of the small cross-sectional area portion, and the length L of the tapered portion 130 in the axial direction of the core shaft may satisfy the following expressions (3) and (2). In the following expressions (3) and (2), the unit of L is mm (millimeter).

$$(FR1/FR2)^{0.25}/L \geq 1.75 \quad (3)$$

$$1 \leq L \leq 3 \quad (2)$$

As a further alternative, the first bending rigidity FR1 of the large cross-sectional area portion, the second bending rigidity FR2 of the small cross-sectional area portion, and the length L of the tapered portion 130 in the axial direction of the core shaft may satisfy the following expressions (1) and (4). In the following expressions (1) and (4), the unit of L is mm (millimeter).

$$(FR1/FR2)^{0.25}/L \geq 0.83 \quad (1)$$

$$1.4 \leq L \leq 3 \quad (4)$$

As a further alternative, the first bending rigidity FR1 of the large cross-sectional area portion, the second bending rigidity FR2 of the small cross-sectional area portion, and the length L of the tapered portion 130 in the axial direction of the core shaft may satisfy the following expressions (5) and (6). In the following expressions (5) and (6), the unit of L is mm (millimeter).

$$(FR1/FR2)^{0.25}/L \geq 1.5 \quad (5)$$

$$1.1 \leq L \leq 3 \quad (6)$$

As a further alternative, the diameter D2 of the large diameter portion, the diameter D1 of the small diameter portion, and the length L of the tapered portion 130 in the axial direction of the core shaft may satisfy the following expressions (7) and (8). In the following expressions (7) and (8), the unit of L is mm (millimeter).

$$(D2/D1)/L \geq 0.83 \quad (7)$$

$$1 \leq L \leq 3 \quad (8)$$

As a further alternative, the diameter D2 of the large diameter portion, the diameter D1 of the small diameter portion, and the length L of the tapered portion 130 in the axial direction of the core shaft may satisfy the following expressions (9) and (8). In the following expressions (9) and (8), the unit of L is mm (millimeter).

$$(D2/D1)/L \geq 1.75 \quad (9)$$

$$1 \leq L \leq 3 \quad (8)$$

As a further alternative, the diameter D2 of the large diameter portion, the diameter D1 of the small diameter portion, and the length L of the tapered portion 130 in the axial direction of the core shaft may satisfy the following expressions (7) and (10). In the following expressions (7) and (10), the unit of L is mm (millimeter).

$$(D2/D1)/L \geq 0.83 \quad (7)$$

$$1.4 \leq L \leq 3 \quad (10)$$

As a further alternative, the diameter D2 of the large diameter portion, the diameter D1 of the small diameter portion, and the length L of the tapered portion 130 in the axial direction of the core shaft may satisfy the following expressions (11) and (12). In the following expressions (11) and (12), the unit of L is mm (millimeter).

$$(D2/D1)/L \geq 1.5 \quad (11)$$

$$1.1 \leq L \leq 3 \quad (12)$$

Here, the ratio (FR1/FR2) of the first bending rigidity of the large cross-sectional area portion 120 and the second bending rigidity of the small cross-sectional area portion 110 in the above-described expression (1), (3), and (5) is calculated as the ratio of the fourth power of the outer diameter using Hooke's law, for example, if the core shaft 100 is formed homogeneously.

The length of the small cross-sectional area portion 110 in the axial direction of the core shaft 100 may be between 3 mm and 15 mm. If the length of the small cross-sectional area portion 110 is 3 mm or larger, sufficient bend of the small cross-sectional area portion 110 may be provided. If the length thereof is 15 mm or smaller, damage due to excessive bend of the small cross-sectional area portion 110 may be reduced or prevented.

In the embodiment, the entire length is 1,900 mm, the axial length of the distal end portion P1 is 100 mm (the axial length of the small cross-sectional area portion 110 is 10 mm, the axial length of the tapered portion 130 is 1 mm, the axial length of the large cross-sectional area portion 120 is 60 mm), the outer diameter of the core shaft main body 150 is 0.35 mm, the outer diameter of the large cross-sectional area portion 120 is 0.10 mm, which corresponds to $\pi/4*0.10^2$ mm$^2$ in cross-sectional area, and the outer diameter of the small cross-sectional area portion 110 is 0.04 mm, which corresponds to $\pi/4*0.04^2$ mm$^2$ in cross-sectional area, as an example.

The material forming the core shaft 100 is not particularly limited as long as the flexibility of the small cross-sectional area portion 110 is secured and the material has antithrombogenicity and biocompatibility. For example, the material forming the core shaft 100 may be stainless steel such as SUS304, a superelastic alloy such as a Ni—Ti alloy, or the like.

The coil body 200 is wound so as to cover at least a part of the outer periphery of the distal end portion P1 that is reduced in cross-sectional area. For example, the coil body 200 is spirally formed using one single wire so that adjacent wires come into contact with each other.

Further, the coil body 200 and the above-described core shaft 100 are not particularly limited as long as they are fixed at the portion of the core shaft 100 excluding the tapered portion 130. However, from the viewpoint of improving the bendability of the distal end portion P1, they may be fixed at the portion of the core shaft 100 excluding the small cross-sectional area portion 110 and the tapered portion 130, e.g., fixed at the portion of the core shaft 100 excluding the small cross-sectional area portion 110, the large cross-sectional area portion 120, and the tapered portion 130. Specifically, as illustrated in FIG. 1, the coil body 200 and the core shaft 100 are brazed at two positions of between a distal end of the coil body 200 and a distal end of the core shaft 100 (see the distal end fixing portion 401), and between a proximal end of the coil body 200 and the connection portion 140 of the core shaft 100 (see the brazing portion 210), for example.

Examples of the brazing material used for brazing the coil body 200 include metals such as an Sn—Pb alloy, a Pb—Ag alloy, an Sn—Ag alloy, an Au—Sn alloy, or the like.

The diameter of the wires forming the coil body 200 may be 0.01 to 0.10 mm, e.g., 0.01 to 0.08 mm. The embodiment exemplifies the coil body 200 having a diameter of 0.06 mm.

The material forming the coil body 200 is not particularly limited as long as the flexibility of the small cross-sectional area portion 110 is secured and the material has antithrombogenicity and biocompatibility. For example, the material forming the coil body 200 may include stainless steel such as SUS316; a superelastic alloy such as a Ni—Ti alloy; a radiopaque metal such as platinum or tungsten, or the like.

The distal fixing portion 401 is a portion where the distal end of the core shaft 100 and the distal end of the coil body 200 are fixed to each other. Specifically, as described above, the distal end fixing portion 401 is a portion where the distal end of the core shaft 100 and the distal end of the coil body 200 are brazed, for example, and the distal end direction thereof is formed in a smoothly bent hemispherical shape by the above-described brazing material in order to prevent damages to the inner wall of a blood vessel when the guide wire 10 advances in the blood vessel.

Next, the use mode of the guide wire 10 will be described. First, a doctor advances the distal end of the guide wire 10 having the bent distal end portion P1 to a closed stenosis site, e.g., a leg artery, a coronary artery, or the like. Thereafter, once the guide wire 10 is inserted in the stenosis site, the distal end portion P1 of the guide wire 10 becomes, in the stenosis lesion, a J-shape starting from the bent shape and passes through the stenosis site. The guide wire 10 passing through the stenosis site is stabilized in the J-shape (the J-shape does not progress to the U-shape) by the tapered portion 130, and passes the stenosis site in such a stabilized J-shape. After passing the stenosis site, a treatment instrument such as a balloon catheter or a stent is conveyed along the guide wire 10 to perform various treatments at the treatment site. After the treatment is completed, the guide wire 10 is withdrawn from the body by retrograding through the blood vessel, and a series of procedures is completed.

As described above, the guide wire 10 with the above-described configuration is able to prevent breakage of the core shaft 100 from the tapered portion 130 as a starting point while suppressing displacement of the bend of the core shaft 100 beyond the tapered portion 130 to the proximal end direction. As a result, the procedure may be performed quickly and securely by smooth operation of the guide wire 10. Without being bound by theory, the effect produced in combination of suppression of stress concentration on the tapered portion 130 during bending when the core shaft 100 and the coil body 200 are not fixed at the tapered portion 130 and bending controllability of the distal end portion P1 by appropriate transition in bending rigidity in the axial direction (see expressions (1) to (12)).

In this manner, the guide wire 10 exerts the above-described effect, and thus can be preferably used as a medical guide wire used for treatment in a blood vessel, for example.

Figure 3:
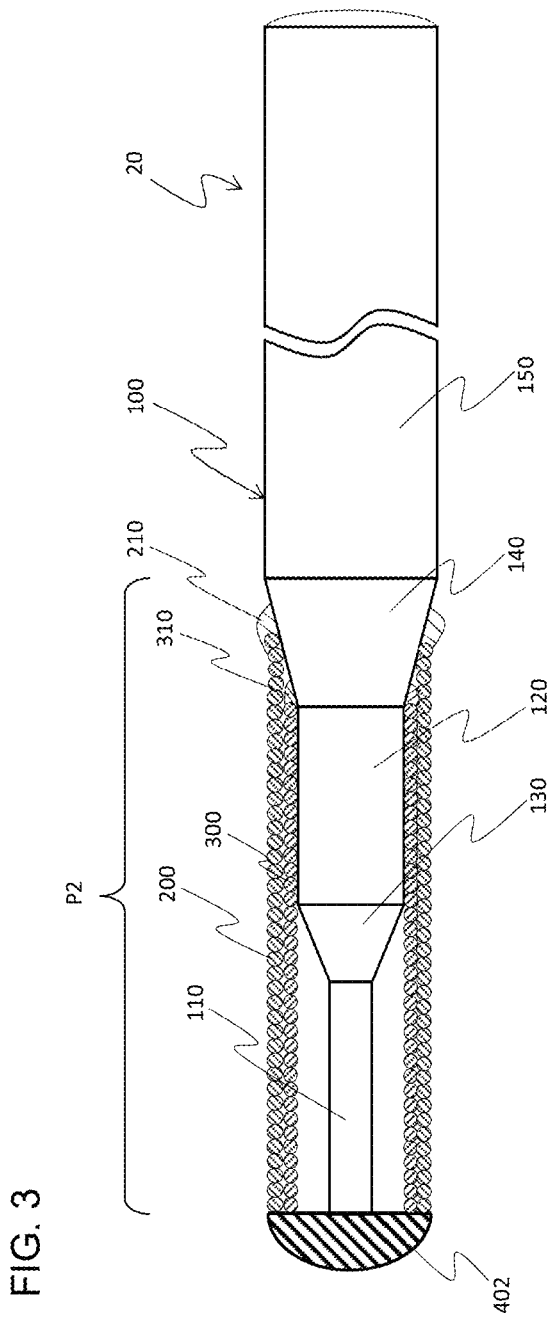
FIG. 3 is a schematic section view illustrating another guide wire, according to some embodiments of the present disclosure.

FIG. 3 is a schematic section view illustrating another guide wire, according to some embodiments of the present disclosure. As illustrated in FIG. 3, a guide wire 20 roughly includes the core shaft 100, the coil body 200, the inner coil body 300, and a distal end fixing portion 402. The guide wire 20 is different from the guide wire 10 in that the inner coil body 300 and the distal end fixing portion 402 are provided. Since the configurations of the core shaft 100, the coil body 200, and other components are the same as those of the above-described guide wire 10, the same parts are represented by the same reference numerals, and detailed description thereof will not be repeated.

The inner coil body 300 is a coil body with a multiple spiral disposed inside the coil body 200 so as to cover the core shaft 100, and is formed as a multiple spiral coil wound using a hollow twisted wire (a bundle of wires in which a plurality of wires are previously twisted mutually), for example, so that the adjacent wires are in contact with each other, and is arranged such that the inner periphery thereof is adjacent to, e.g., in contact with, the outer periphery of the large cross-sectional area portion 120.

In addition, the inner coil body 300 and the core shaft 100 are not particularly limited as long as they are fixed at a portion excluding the tapered portion 130, the portion on the core shaft 100 in the proximal end direction than the tapered portion 130, and at the distal end fixing portion 402. For example, a portion on the core shaft 100 in the proximal end direction than the large cross-sectional area portion 120 and at the distal end fixing portion 402. Specifically, as illustrated in FIG. 3, the inner coil body 300 and the core shaft 100 are brazed at two positions of between a distal end of the inner coil body 300 and the distal ends of the core shaft 100 and the coil body 200 (see the distal end fixing portion 402), and between the proximal end of the inner coil body 300 and the connection part 140 of the core shaft 100 (see the brazing portion 310), for example.

Note that, the brazing material used for brazing the inner coil body 300 may include the same brazing material as the brazing material used for brazing the coil body 200 in the guide wire 10, for example.

The diameter of the wires forming the inner coil body 300 may be 0.01 to 0.05 mm, e.g., 0.01 to 0.04 mm. The embodiment exemplifies the inner coil body 300 having a diameter of 0.030 mm.

The material of the wire forming the inner coil body 300 may include the same material as the material of the wire of the coil body 200 described above in the guide wire 10, for example.

The distal fixing portion 402 is a portion where the distal end of the core shaft 100, the distal end of the coil body 200, and the inner coil body 300 are fixed to one another. Specifically, as described above, the distal end fixing portion 402 is a portion where the distal end of the core shaft 100, the distal end of the coil body 200, and the distal end of the inner coil body 300 are brazed, and the distal end side thereof is formed in a smoothly bent hemispherical shape by the brazing material, for example.

Since the use mode of the guide wire 20 is the same as that of the guide wire 10, the description of the guide wire 10 is not repeated.

In this manner, in the guide wire 20, the core shaft 100 and the inner coil body 300 are fixed at a portion excluding the tapered portion 130, the portion on the core shaft 100 in the proximal end direction than the tapered portion 130, and at the distal end fixing portion 402. Therefore, even if the core shaft 100 is broken at the small cross-sectional area portion 110 or the tapered portion 130, the broken portion is connected to other portions of the guide wire 20 through the inner coil body 300, which prevents splitting or detachment of these portions, allowing the procedure to be performed more safely.

Note that the present disclosure is not limited to the configurations of the above-described embodiments, but is defined by the terms of the claims and is intended to include any modifications within the scope and meaning equivalent to the terms of the claims.

For example, the above embodiments have described the guide wires 10, 11, 20 in which the rigidity of each of the coil body 200 and the inner coil body 300 is uniform. However, the guide wire may be formed such that the bending rigidity of the coil body and/or the inner coil body is higher in the proximal end direction than that in the distal end direction of the tapered portion in the axial direction of the core shaft. Thereby, the rigidity of the entire guide wire at the tapered portion as a boundary, and enhance bending displacement suppression property. The coil body and the inner coil body as described above include those in which the wire diameters of the constituent wires are different before and after the tapered portion and in which the constituent wires in a portion in the proximal end direction than the tapered portion as a starting point are integrated by welding, soldering, or the like, for example.

Further, the above embodiments have described the guide wires 10, 20 in which the bending rigidity FR1 and FR2 are calculated using Hooke's law. However, the bending rigidity FR1 and FR2 may be values obtained by actual measurement, or by a method other than the above-described methods.

The above embodiments have described the guide wires 10 in which the core shaft 100 and the coil body 200 are brazed, and the guide wire 20 in which the core shaft 100, the coil body 200, and the inner coil body 300 are brazed. However, the guide wire may be formed such that the above-described members are fixed by another known technique such as arc welding or resistance welding.

Further, the above embodiments have described the guide wires 10 in which the core shaft 100 and the coil body 200 are fixed at the distal end fixing portion 401 and at the brazing portion 210, and the guide wire 20 in which the core shaft 100 and the inner coil body 300 are fixed at the distal end fixing portion 402 and at the brazing portion 310. However, the guide wire may be formed such that the above-described members are fixed at any one or two or more portions as long as such portions exclude the tapered portion.

Moreover, the above-described embodiments have described the guide wires 10, 11, 20 in which the coil body 200 is formed as a single spiral coil and the inner coil body 300 is formed as a multiple spiral coil. However, the coil body may be formed as a multiple spiral coil, and the inner coil body may be formed as a single spiral coil.

Further, the above-described embodiments have exemplified the guide wires 10, 11, 20 including the connection portion 140 between the large cross-sectional area portion 120 and the core shaft main body 150 of the core shaft 100, 101. However, the guide wire may be formed such that the large cross-sectional area portion is a part of the core shaft main body (a guide wire in which the large cross-sectional area portion and the core shaft main body have the same cross-sectional area and are continuous with each other).

EXAMPLE

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, Examples will be specifically described, but the disclosure is not limited to these examples. These examples show the results regarding guide wires including a core shaft, a coil body, and a distal end fixing portion as described above as the guide wire 10.
<Guide Wire>

Regarding the specifications of each guide wire to be evaluated, Table 1 shows the outer diameter D1 of the small cross-sectional area portion, the outer diameter D2 of the large cross-sectional area portion, the length L of the tapered portion in the axial direction, the value of (FR1/FR2)/L, and $(FR1/FR2)^{0.25}/L$. Note that the above FR1 and FR2 have the same meaning as those in the above-described expression (1), (3), and (5). Other specifications are as follows.
[Core Shaft]
Material: SUS304
Axial length
   Entire length: 1,900 mm
   Distal end portion: 100 mm
   Small cross-sectional area portion: 10 mm
   Tapered portion: Shown in Table 1
   Large cross-sectional area portion: 60 mm
Diameter
   Core shaft main body: 0.35 mm
   Small cross-sectional area portion: Shown in Table 1
   Large cross-sectional area portion: Shown in Table 1
[Coil Body]
Material: SUS304
Diameter: 0.06 mm
<Evaluation>

Using each of the guide wires shown in Table 1, the bending displacement suppression property was evaluated by the following method. The results are shown in Table 1 and FIG. 5 and in Table 1 and FIG. 6. In Table 1, the bending rigidity ratio (FR1/FR2) is calculated using bending rigidity obtained by Hooke's law.
[Bending Displacement Suppression Property]

There were preliminarily prepared a guide wire having a portion in the distal end direction bent in a U-shape at a portion 1 mm from the distal end of the small cross-sectional area portion of the core shaft as a starting point (bent section), and a transparent acrylic pipe filled with gel having hardness of 3,000 to 4,000 gf/cm$^2$, as a simulated lesion.

Next, using the guide wire and the acrylic pipe, each guide wire was slowly inserted into the acrylic pipe so that the guide wire was not deformed, and temporarily stopped at the initial position.

Next, the guide wire was pushed from the initial position at a speed of 1 cm/sec, and the displacement of the bent section was visually observed at the push-in position after pushing 10 cm from the initial position.

Figure 4A:
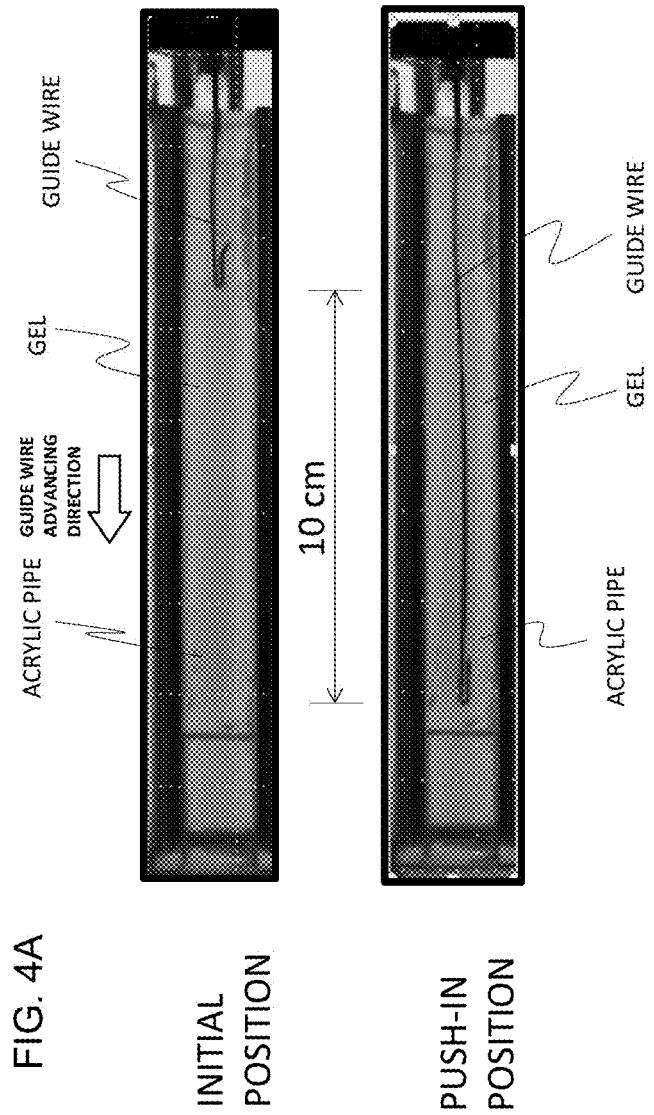
FIG. 4A is a schematic view illustrating a bent state of a guide wire, and is the schematic view illustrating the guide wire having a preferable bending displacement suppression property.
Figure 4B:
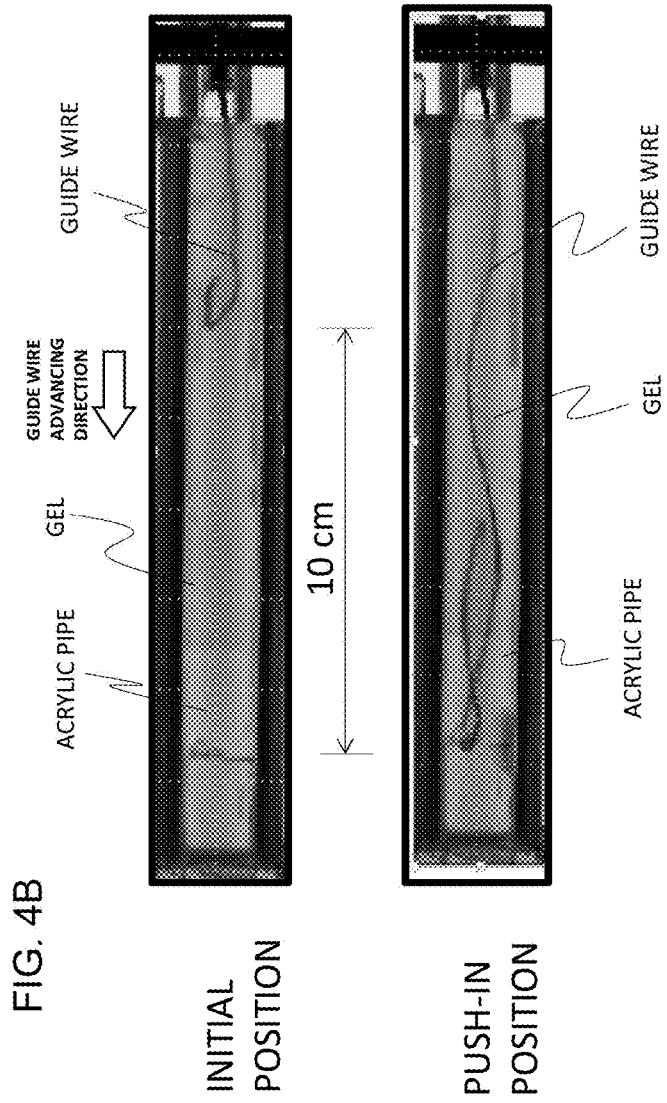
FIG. 4B is a schematic view illustrating a bent state of a guide wire, and is the schematic view illustrating the guide wire having an inferior bending displacement suppression property.

Here, if it is not visually recognized that the bent section is displaced toward the proximal end direction of the guide wire (see FIG. 4A, for example), the bending displacement suppression property was evaluated as preferable "A", while if the displacement is visible (for example, see FIG. 4B, for example), the bending displacement suppression property was evaluated as inferior "B".

TABLE 1

|  | Outer diameter D1 of small cross-sectional area portion [mm] | Outer diameter D2 of large cross-sectional area portion [mm] | Length L of tapered portion [mm] | (FR1/FR2)/L [1/mm] | (FR1/FR2)$^{0.25}$/L [1/mm] | Bending displacement suppression property |
|---|---|---|---|---|---|---|
| Example 1 | 0.040 | 0.074 | 1.0 | 11.5 | 1.85 | A |
| Example 2 | 0.043 | 0.083 | 1.1 | 12.8 | 1.75 | A |

TABLE 1-continued

|  | Outer diameter D1 of small cross-sectional area portion [mm] | Outer diameter D2 of large cross-sectional area portion [mm] | Length L of tapered portion [mm] | (FR1/ FR2)/L [1/mm] | (FR1/ FR2)$^{0.25}$/L [1/mm] | Bending displacement suppression property |
|---|---|---|---|---|---|---|
| Example 3 | 0.043 | 0.084 | 1.0 | 15.2 | 1.95 | A |
| Example 4 | 0.040 | 0.082 | 1.0 | 17.3 | 2.05 | A |
| Example 5 | 0.043 | 0.090 | 1.1 | 17.3 | 1.90 | A |
| Example 6 | 0.040 | 0.091 | 1.4 | 19.5 | 1.63 | A |
| Example 7 | 0.043 | 0.090 | 1.4 | 14.1 | 1.60 | A |
| Example 8 | 0.043 | 0.098 | 1.0 | 26.3 | 2.28 | A |
| Example 9 | 0.043 | 0.097 | 1.1 | 24.5 | 2.05 | A |
| Example 10 | 0.043 | 0.097 | 1.1 | 24.5 | 2.05 | A |
| Example 11 | 0.043 | 0.100 | 2.8 | 10.6 | 0.83 | A |
| Example 12 | 0.043 | 0.118 | 1.0 | 56.3 | 2.74 | A |
| Example 13 | 0.043 | 0.119 | 1.1 | 52.3 | 2.52 | A |
| Example 14 | 0.043 | 0.119 | 1.0 | 59.1 | 2.77 | A |
| Example 15 | 0.043 | 0.130 | 1.2 | 70.6 | 2.52 | A |
| Example 16 | 0.043 | 0.137 | 1.0 | 100.6 | 3.19 | A |
| Example 17 | 0.041 | 0.137 | 1.1 | 114.0 | 3.04 | A |
| Example 18 | 0.051 | 0.108 | 1.1 | 17.5 | 1.93 | A |
| Example 19 | 0.051 | 0.109 | 1.2 | 17.3 | 1.78 | A |
| Example 20 | 0.051 | 0.110 | 1.1 | 19.9 | 1.96 | A |
| Example 21 | 0.054 | 0.117 | 1.1 | 20.8 | 1.97 | A |
| Example 22 | 0.054 | 0.117 | 1.0 | 22.2 | 2.17 | A |
| Example 23 | 0.054 | 0.118 | 1.1 | 21.0 | 1.99 | A |
| Example 24 | 0.050 | 0.129 | 1.1 | 19.7 | 1.95 | A |
| Example 25 | 0.050 | 0.128 | 1.0 | 20.2 | 2.13 | A |
| Example 26 | 0.050 | 0.130 | 1.0 | 21.6 | 2.17 | A |
| Example 27 | 0.031 | 0.085 | 1.5 | 38.0 | 1.83 | A |
| Example 28 | 0.034 | 0.085 | 1.0 | 40.8 | 2.50 | A |
| Example 29 | 0.034 | 0.085 | 1.8 | 24.7 | 1.56 | A |
| Example 30 | 0.029 | 0.093 | 1.4 | 76.1 | 2.29 | A |
| Example 31 | 0.033 | 0.093 | 1.0 | 61.8 | 2.82 | A |
| Example 32 | 0.031 | 0.093 | 1.2 | 70.4 | 2.50 | A |
| Example 33 | 0.037 | 0.093 | 1.0 | 39.1 | 2.51 | A |
| Example 34 | 0.038 | 0.093 | 1.5 | 24.4 | 1.53 | A |
| Example 35 | 0.039 | 0.093 | 1.2 | 27.0 | 1.99 | A |
| Comparative Example 1 | 0.043 | 0.054 | 1.8 | 1.4 | 0.70 | B |
| Comparative Example 2 | 0.040 | 0.054 | 0.7 | 4.5 | 1.93 | B |
| Comparative Example 3 | 0.040 | 0.053 | 1.1 | 2.5 | 1.20 | B |
| Comparative Example 4 | 0.043 | 0.058 | 1.2 | 2.4 | 1.09 | B |
| Comparative Example 5 | 0.043 | 0.058 | 1.1 | 3.2 | 1.25 | B |
| Comparative Example 6 | 0.043 | 0.058 | 1.3 | 2.5 | 1.04 | B |
| Comparative Example 7 | 0.041 | 0.060 | 0.9 | 5.0 | 1.63 | B |
| Comparative Example 8 | 0.042 | 0.062 | 1.2 | 4.1 | 1.23 | B |
| Comparative Example 9 | 0.043 | 0.058 | 1.0 | 3.5 | 1.37 | B |
| Comparative Example 10 | 0.040 | 0.064 | 1.0 | 6.8 | 1.60 | B |
| Comparative Example 11 | 0.040 | 0.065 | 1.1 | 6.6 | 1.48 | B |
| Comparative Example 12 | 0.043 | 0.088 | 1.1 | 5.4 | 1.44 | B |
| Comparative Example 13 | 0.043 | 0.074 | 1.0 | 9.2 | 1.72 | B |
| Comparative Example 14 | 0.045 | 0.075 | 1.2 | 6.8 | 1.39 | B |

Figure 5:
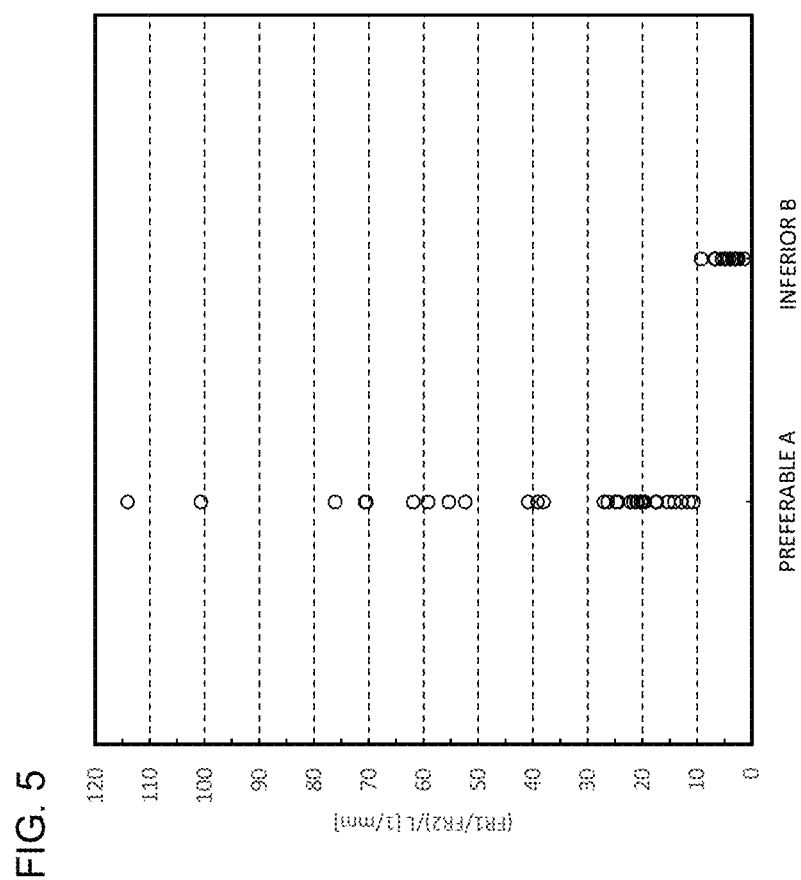
FIG. 5 is a graph in which the evaluation results of a fourth column of Table 1 are plotted.
Figure 6:
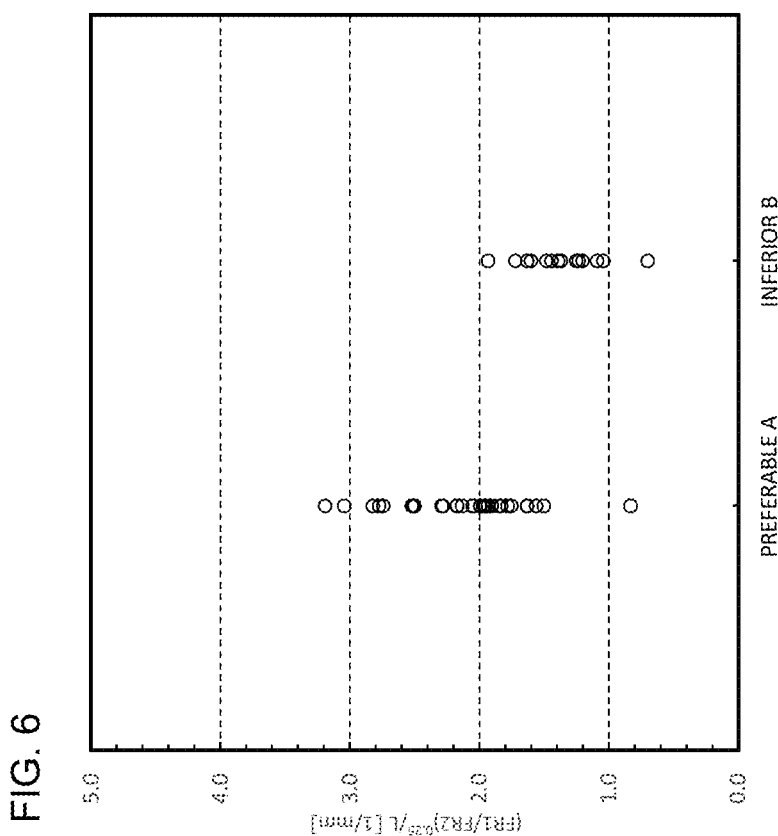
FIG. 6 is a graph in which the evaluation results of a fifth column of Table 1 are plotted.

As can be seen from the results in Table 1 and FIGS. 5 and 6, the bending displacement suppression property was superior or preferable "A" in all examples. However, it was inferior "B" in all comparative examples.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Obviously, numerous modifications and variations of the present invention are possible in light of the above teachings. It is therefore to be understood that within the scope of the appended claims, the invention may be practiced otherwise than as specifically described herein.

The invention claimed is:

1. A guide wire, comprising:
a core shaft that includes a distal end portion stepwise decreasing in cross-sectional area toward a distal end direction;
a coil body that is wound to cover at least a part of an outer periphery of the cross-sectional area-decreased distal end portion; and
a distal end fixing portion that fixes a distal end of the core shaft, and a distal end of the coil body to each other,
wherein the distal end portion of the core shaft includes:
a small cross-sectional area portion adjacent to the distal end fixing portion,
a large cross-sectional area portion further in a proximal end direction than the small cross-sectional area portion and has a larger cross-sectional area than the small cross-sectional area portion, and
a tapered portion between the small cross-sectional area portion and the large cross-sectional area portion, the tapered portion gradually increasing in cross-sectional area from the small cross-sectional area portion to the larger cross-sectional area of the large cross-sectional area portion,
the core shaft and the coil body are fixed at a portion of the core shaft excluding the tapered portion, and
a first bending rigidity FR1 of the large cross-sectional area portion, a second bending rigidity FR2 of the small cross-sectional area portion, and a length L of the tapered portion in an axial direction of the core shaft satisfy the following expressions (1) and (2):

$$(FR1/FR2)^{0.25}/L \geq 0.83 \qquad (1)$$

$$1 \leq L \leq 3 \qquad (2)$$

(in the above expressions (1) and (2), the unit of L is mm (millimeter)).

2. The guide wire according to claim 1, wherein a length of the small cross-sectional area portion in the axial direction of the core shaft is between 3 mm and 15 mm.

3. The guide wire according to claim 1, wherein a section shape of the small cross-sectional area portion orthogonal to the axial direction of the core shaft has a flat shape.

4. The guide wire according to claim 1, further comprising an inner coil body that is a multiple spiral coil, and inside the coil body so as to cover the core shaft, the core shaft and the inner coil body are fixed at a portion excluding the tapered portion, the portion where the core shaft and inner coil body are fixed being on the core shaft further in a proximal end direction than the tapered portion and at the distal end fixing portion.

5. The guide wire according to claim 4, wherein the core shaft includes a core shaft main body and a connection portion between the core shaft main body and the large cross-sectional area portion, and the core shaft and the inner coil body are fixed at the connection portion.

6. The guide wire according to claim 1, wherein the core shaft includes a core shaft main body and a connection portion between the core shaft main body and the large cross-sectional area portion, and the core shaft and the coil body are fixed at the connection portion.

7. The guide wire according to claim 1, wherein the large cross-sectional area portion has a constant cross-sectional area.

8. The guide wire according to claim 7, wherein a section shape of the large cross-sectional area portion is circular.

9. The guide wire according to claim 1, wherein the expression (1) is defined:

$$(FR1/FR2)^{0.25}/L \geq 1.75 \qquad (3)$$

(in the above expressions (3) and (2), the unit of L is mm (millimeter)).

10. The guide wire according to claim 1, wherein the expression (2) is defined:

$$1.4 \leq L \leq 3 \qquad (4)$$

(in the above expressions (1) and (4), the unit of L is mm (millimeter)).

11. The guide wire according to claim 1, wherein the expressions (1) and (2) are defined respectively:

$$(FR1/FR2)^{0.25}/L \geq 1.5 \qquad (5)$$

$$1.1 \leq L \leq 3 \qquad (6)$$

(in the above expressions (5) and (6), the unit of L is mm (millimeter)).

12. A guide wire, comprising:
a core shaft that includes a distal end portion stepwise decreasing in diameter toward a distal end direction;
a coil body that is wound to cover at least a part of an outer periphery of the diameter-decreased distal end portion; and
a distal end fixing portion that fixes a distal end of the core shaft, and a distal end of the coil body to each other,
wherein the distal end portion of the core shaft includes:
a small diameter portion adjacent to the distal end fixing portion,
a large diameter portion further in a proximal end direction than the small diameter portion and has a larger diameter than the small diameter portion, and
a tapered portion between the small diameter portion and the large diameter portion, the tapered portion gradually increasing in diameter from the small diameter portion to the larger diameter of the large diameter portion,
the core shaft and the coil body are fixed at a portion of the core shaft excluding the tapered portion, and
a diameter D2 of the large diameter portion, a diameter D1 of the small diameter portion, and a length L of the tapered portion in an axial direction of the core shaft satisfy the following expressions (7) and (8):

$$(D2/D1)/L \geq 0.83 \qquad (7)$$

$$1 \leq L \leq 3 \qquad (8)$$

(in the above expressions (7) and (8), the unit of L is mm (millimeter)).

13. The guide wire according to claim 12, wherein a length of the small diameter portion in the axial direction of the core shaft is between 3 mm and 15 mm.

14. The guide wire according to claim 12, wherein a section shape of the small diameter portion orthogonal to the axial direction of the core shaft has a flat shape.

15. The guide wire according to claim 12, further comprising an inner coil body that is a multiple spiral coil, and inside the coil body so as to cover the core shaft, wherein the core shaft and the inner coil body are fixed at a portion excluding the tapered portion, the portion where the core shaft and inner coil body are fixed being on the core shaft further in a proximal end direction than the tapered portion and at the distal end fixing portion.

16. The guide wire according to claim 15, wherein the core shaft includes a core shaft main body and a connection portion between the core shaft main body and the large diameter portion, and the core shaft and the inner coil body are fixed at the connection portion.

17. The guide wire according to claim 12, wherein the core shaft includes a core shaft main body and a connection portion between the core shaft main body and the large diameter portion, and the core shaft and the coil body are fixed at the connection portion.

18. The guide wire according to claim 12, wherein the expression (7) is defined:

$$(D2/D1)/L \geq 1.75 \qquad (9)$$

(in the above expressions (9) and (8), the unit of L is mm (millimeter)).

19. The guide wire according to claim 12, wherein the expression (8) is defined:

$$1.4 \leq L \leq 3 \qquad (10)$$

(in the above expressions (7) and (10), the unit of L is mm (millimeter)).

20. The guide wire according to claim 12, wherein the expressions (7) and (8) are defined respectively:

$$(D2/D1)/L \geq 1.5 \qquad (11).$$

$$1.1 \leq L \leq 3 \qquad (12)$$

(in the above expressions (11) and (12), the unit of L is mm (millimeter)).

* * * * *